(12) United States Patent
Basler et al.

(10) Patent No.: US 7,985,119 B2
(45) Date of Patent: Jul. 26, 2011

(54) BLANK FOR THE PRODUCTION OF A DENTAL SHAPED BODY AND METHOD OF PRODUCING SAID SHAPED BODY

(75) Inventors: Franz Basler, Laudenbach (DE); Peter Fornoff, Reichelsheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 1418 days.

(21) Appl. No.: 11/304,536

(22) Filed: Dec. 16, 2005

(65) Prior Publication Data
US 2006/0141250 A1 Jun. 29, 2006

(30) Foreign Application Priority Data
Dec. 23, 2004 (DE) .................. 10 2004 063 417

(51) Int. Cl.
*B24B 49/00* (2006.01)
(52) U.S. Cl. .............. 451/5; 451/9; 451/28; 451/54; 451/58; 433/202.1; 433/223; 433/72
(58) Field of Classification Search .............. 451/5, 8, 451/9, 22, 28, 54, 57, 58; 433/201.1, 49, 433/223, 202.1, 72, 73
See application file for complete search history.

(56) References Cited

U.S. PATENT DOCUMENTS

| | | | |
|---|---|---|---|
| 3,665,493 A | 5/1972 | Glowzewski et al. | |
| 4,615,678 A | 10/1986 | Moermann et al. | |
| 4,988,297 A | 1/1991 | Lazzara et al. | |
| 5,092,022 A | 3/1992 | Duret | |
| 5,273,429 A | 12/1993 | Rekow et al. | |
| 5,342,696 A | 8/1994 | Eidenbenz et al. | |
| 5,359,511 A | 10/1994 | Schroeder et al. | |
| 5,378,091 A | 1/1995 | Nakamura | |
| 5,556,278 A | 9/1996 | Meitner | |
| 5,716,215 A | 2/1998 | Blacklock | |

(Continued)

FOREIGN PATENT DOCUMENTS
AU 762679 B2 7/2003
(Continued)

OTHER PUBLICATIONS

Brian K.S. Kucey et al., "The Procera Abutment—The Fifth Generation Abutment for Dental Implants," Journal of Canadian Dental Association, vol. 66, No. 8, pp. 445-449 (Sep. 2000).

(Continued)

*Primary Examiner* — Eileen P. Morgan
(74) *Attorney, Agent, or Firm* — Fitzpatrick, Cella, Harper & Scinto (57) ABSTRACT

A blank and method for the production of dental shaped bodies in machining equipment having at least two tools located in the machining chamber of the machining equipment, including a corpus of tooth restoration material, from which the shaped body can be carved by means of at least one of at least two tools by material removal. The blank exhibits at least two gages, each of which is in the form of a recess, the geometry of which is such that the tool selected for the cutting operation can be recognized by means of at least one of the gages by reference to its outer contour, the at least two gages being disposed on the blank in such a way that they can be simultaneously engaged by the at least tools when the blank is clamped in the machining equipment for carving purposes.

5 Claims, 8 Drawing Sheets

U.S. PATENT DOCUMENTS

| | | | |
|---|---|---|---|
| 5,788,494 | A | 8/1998 | Phimmasone |
| 5,846,079 | A | 12/1998 | Knode |
| 5,989,029 | A | 11/1999 | Osorio et al. |
| 6,126,445 | A | 10/2000 | Willoughby |
| 6,142,782 | A | 11/2000 | Lazarof |
| 6,224,371 | B1 | 5/2001 | De Luca |
| 6,231,342 | B1 | 5/2001 | Osorio et al. |
| 6,354,836 | B1 | 3/2002 | Panzera et al. |
| 6,394,880 | B1 * | 5/2002 | Basler et al. ............ 451/28 |
| 6,398,554 | B1 | 6/2002 | Perot et al. |
| 6,482,284 | B1 | 11/2002 | Reidt et al. |
| 6,485,305 | B1 | 11/2002 | Pfeiffer |
| 6,640,150 | B1 | 10/2003 | Persson et al. |
| 6,666,684 | B1 | 12/2003 | Names |
| 6,788,986 | B1 | 9/2004 | Traber et al. |
| 6,968,247 | B2 | 11/2005 | Rathke et al. |
| 6,970,760 | B2 | 11/2005 | Wolf et al. |
| 7,086,863 | B2 | 8/2006 | Van der Zel |
| 7,226,338 | B2 * | 6/2007 | Duncan et al. ............ 451/6 |
| 2002/0090592 | A1 | 7/2002 | Riley et al. |
| 2003/0073394 | A1 | 4/2003 | Reidt et al. |
| 2006/0106484 | A1 | 5/2006 | Saliger et al. |
| 2006/0292527 | A1 | 12/2006 | Basler et al. |
| 2007/0050072 | A1 | 3/2007 | Schwotzer |
| 2009/0273108 | A1 | 11/2009 | Koebel et al. |

FOREIGN PATENT DOCUMENTS

| | | |
|---|---|---|
| DE | 19654055 A1 | 6/1998 |
| DE | 19733161 A1 | 2/1999 |
| DE | 103 30 758 | 2/2005 |
| DE | 102006052027 A1 | 5/2008 |
| EP | 0 455 854 | 4/1994 |
| EP | 0455854 | 4/1994 |
| EP | 0850601 A2 | 7/1998 |
| EP | 0904743 A2 | 3/1999 |
| EP | 1023876 A2 | 8/2000 |
| EP | 1062916 A2 | 12/2000 |
| EP | 1252867 A1 | 10/2002 |
| EP | 1067880 B1 | 10/2003 |
| EP | 1658825 A1 | 5/2006 |
| JP | 10-277059 A | 10/1998 |
| WO | 99/13796 | 3/1999 |
| WO | 99/47065 A1 | 9/1999 |
| WO | 01/35854 | 5/2001 |
| WO | 0135854 | 5/2001 |
| WO | 03/007834 A1 | 1/2003 |
| WO | 03/024352 A1 | 3/2003 |
| WO | 2004/060197 A1 | 7/2004 |
| WO | 2005/002463 A1 | 1/2005 |

OTHER PUBLICATIONS

European Patent Office, "Internationaler Vorlaufiger Bericht Uber Die Patentierbarkeit" issued in International Application No. PCT/EP2008/060043, 6 pages, Oct. 19, 2009 (and English translation thereof).

European Patent Office, "Schriftlicher Bescheid Der Internationalen Recherchenbehorde" in connection with International Application No. PCT/EP2009/053999, 6 pages, Oct. 3, 2010 (and English translation thereof).

At least partial English translation of Office Action issued Feb. 12, 2009, by the German Patent Office in connection with International Application No. PCT/EP2009/053999, 2 pages.

U.S. Patent and Trademark Office, Office Action dated Apr. 20, 2009, in connection with U.S. Appl. No. 10/557,153, 11 pages.

U.S. Patent and Trademark Office, Office Action dated Oct. 14, 2009, in connection with U.S. Appl. No. 10/557,153, 12 pages.

U.S. Patent and Trademark Office, Office Action dated Mar. 11, 2010, in connection with U.S. Appl. No. 10/557,153, 13 pages.

U.S. Patent and Trademark Office, Office Action dated Nov. 23, 2010, in connection with U.S. Appl. No. 10/557,153, 16 pages.

* cited by examiner

BLANK FOR THE PRODUCTION OF A DENTAL SHAPED BODY AND METHOD OF PRODUCING SAID SHAPED BODY

TECHNICAL FIELD

The invention relates to a blank for the production of dental shaped bodies, and to a process for the production of a dental shaped body.

DESCRIPTION OF THE RELATED ART

EP 0 160 797 discloses a blank for the production of dental shaped bodies, which blank is made up of a handle and a corpus of different materials. A reference surface on the handle can be formed in such a way that control information for the machining process depending on the characteristics of the blank, can be derived.

Another blank for the production of dental shaped bodies is disclosed by DE 196 12 699. Here again, recognition of the type of blank from the geometrical shape of its contours is disclosed.

EP 0 455 854 discloses a blank, from which there can be carved a prosthetic item to be administered to the patient, on the one hand, and an additional retaining or supporting body, on the other hand. A recess is carved into the prosthetic item, which is shaped in such a way that it can be fitted on the retaining or supporting body.

The position of the abrasion-prone tools used for machining the blank is adjusted such that the tools are moved to engage defined reference surfaces on the blank. These reference surfaces can be on the handle, as shown in EP 0 160 797 or they can, as shown in DE 196 12 699, be positioned on the corpus of the blank or on its own reference body, which is attached to the blank at more or less arbitrary places.

WO 01/35854 discloses a blank having a recess for the accommodation of an indexing peg. Furthermore, a reference surface is provided, by means of which the overall dimensions of the tools can be measured.

The reference surfaces that are provided in the prior art are only suitable for purposes of adjustment of the tool relative to the blank.

It is an object of the invention to make it possible to reliably analyze or identify the tool equipment and/or the type and state of wear of the tool used in the machining equipment employed for machining the blank. In particular, it is intended to provide means of recognizing incorrect tool setups in grinding machines using different types of tool at the same time.

SUMMARY OF THE INVENTION

This object is achieved by the invention with the features in the characterizing parts of the independent claims, advantageous developments being defined in the respective subclaims.

One way of achieving the object of the invention is given by a blank for the production of dental shaped bodies which is machined in machining equipment by at least two tools located in the machining chamber of the machining equipment. The blank comprises a corpus of tooth restoration material, from which the shaped body can be carved by means of at least one of the at least two tools by material removal. Furthermore, the blank has at least two gages, each of which is in the form of a recess, the geometry of the recesses being such that the tool used for machining is identifiable on the basis of its outer contour by means of the at least one gage, the at least two gages being disposed on the blank such that they can be simultaneously engaged by the at least two tools when the blank is clamped in the machining equipment for machining thereof.

This has the advantage that the tools can be checked by the blank that is already clamped in the machine, such checking being effected in a single pass and thus with considerable time saving.

An alternative embodiment is represented by a blank which is processed in machining equipment for the production of dental shaped bodies and comprises a corpus of tooth restoration material from which the shaped body can be carved by means of at least one of the tools by material removal, which blank has at least one gage in the form of a recess, the geometry of the recess being such that a tool selected for machining and tapered toward its machining edge can be detected on account of its outer contour by means of the gage. The recess tapers to its base and the aperture angle of the conical envelope of the tapered recess is at least equal to the aperture angle of the conical envelope of the tool tapered toward its machining edge.

This embodiment allows tools which taper toward their machining tip to be detected particularly well and reliably.

According to another alternative embodiment a blank is provided for the production of dental shaped bodies in machining equipment, comprising a corpus of tooth restoration material from which the shaped body can be carved by means of at least one tool by material removal, which blank exhibits at least one gage in the form of a recess, the geometry of said recess being such that the tool selected for machining can be detected on account of its outer contour by means of the gage, another recess being present for indexing the blank and for directional positioning of the blank in the machining equipment.

Such a blank enables unambiguous positioning of the blank in the machining equipment and faulty positioning is almost impossible. Furthermore, indexing allows for recognition of the type of blank clamped in the machine by the machining equipment itself, and the selection of a blank which is unsuitable for the current purpose is thus avoided.

These alternative embodiments of the blank can be further improved by one or more of the following preferred developments.

The gage is advantageously assigned to an ideal outer contour of a first tool, as this makes it possible to identify the tool that corresponds to the gage. In addition, another tool having a different ideal outer contour from that of the first tool can be distinguished with the aid of the same gage. In this way, not only can the tool matching the gage be selected, but different tools can be distinguished from each other.

An advantageous shape of such a gage can be a recess, in which the ideal outer contour of the first tool engages. Such engagement can be made possible, for example, by forming the recess such that the tool having an ideal outer contour fits it exactly.

It is particularly advantageous if at least one of the gages in the blank comprises a recess corresponding to an ideal outer contour of a first cylindrical mold having a first cutting edge diameter, the diameter of which is smaller then the ideal outer contour of a second cylindrical mold having a second cutting edge diameter. In this way two cylindrical tools of different thicknesses can be differentiated in a particularly easy manner.

Another advantageous shape of such a recess serving as a gage is a recess that is tapered in correspondence with the ideal outer contour of a first tapered tool, with the recess tapered to a diameter that is smaller than the smallest diameter of the ideal outer contour of a second cylindrical tool. In this way, it is also possible to distinguish tools of different geometry from each other. This principle is naturally also transferable to any other tool shapes, and can be used, for example, on tools having a rounded end.

Advantageously, the recess of at least one of the gages is designed such that it can detect a stepwise tapering tool. Such tools are being used to an increasing extent by reason of their good machining properties when working on dental ceramics, and the possibility of recognition of these tools is thus becoming increasingly important.

Advantageously, the gage is in the form of a groove or bore, since these are particularly easy to create.

It is particularly advantageous if at least one of the recesses of the gages in the blank contains at least two subregions, the second subregion lying within the first subregion and the subregions form a cross section which decreases toward the base of the recess. A gage that is designed in such a manner is found to be particularly versatile, since very many tools can be distinguished from each other in view of the plurality of subregions that are present.

It is especially advantageous when the gage is designed in such a way that when the tool to which the gage is assigned is moved into the gage, the actual state of the dimensions of the respective tool can be identified such that the degree of wear of the tool can be assessed and, for example, a certain minimum tool quality can be prescribed. A further advantage is that it is possible to effect a reliable analysis or identification of the tool setup and/or the type of tool used in the machining equipment employed for machining the blank, and the wear condition of said tool.

Another advantage is gained when the blank comprises a handle for mounting and/or positioning the corpus of the blank in a machining device and when the gage is provided on said handle, since thereby the gage will remain effective throughout the entire machining operation and the corresponding tools can be checked on a continuous basis. Such identification of poor quality tools or incorrect setups will be contributory, for example, to preventing tool fracture during machining.

Alternatively, at least one gage can be on the handle or on the corpus of the blank or on a reference portion, by which means special production characteristics can be taken into consideration. In addition, at least one gage can be at least two of the said positions.

If the gage is designed as a universal gage for prospective tools, advantageously various tool geometries can be checked with only one gage. A gage is considered to be a universal gage if the geometrical shape of several tools can be checked with the aid of this one gage. This requires that the shape geometry itself consists of several individual shape geometries, of which each corresponds to the tool geometry of its respective tool. By this means, it is not only possible for a more extensive tool setup to be examined with the aid of only one gage, but it is also possible to examine the degree of wear of a number of, or if necessary all, tools with the aid of just one gage. In this way, it will be possible to detect incorrect setup with minimum elaboration. Instead of using only one universal gage, several universal gages of identical or different geometrical shapes can be used if this would seem necessary, for production or control reasons for example, in order to enable the tool to be driven to the blank more quickly, for instance.

Advantageously, at least two of the gages are disposed on the handle of the blank diametrically opposed to each other. This affords good accessibility of the gages when use is made of the blank in machining equipment in which at least two tools are employed if the tools are disposed substantially symmetrically on each side of the blank.

Another aspect of the invention relates to a method for the production of dental shaped bodies having a corpus of tooth restoration material. The entire shaped body is carved from the blank, in machining equipment, by material removal by means of at least two tools, the tools selected for carving being simultaneously checked, before use, with regard to their outer contour with the aid of the at least two gages provided on the blank. The advantage gained here is the saving of time for recognition of the tools with regard to the outer contour thereof.

A further advantage results if the tool dedicated to the gage is driven into the gage and the current deviation of the assigned tool from the ideal is determined, since information about the momentary tool condition can be determined in this manner each and every time the tool engages the gage(s). This can be done several times during an operation sequence. Thus an optimal condition and, therefore, high quality of the shaped body can be guaranteed.

Another advantage results when the degree of deviation of the actual condition of the tool from the ideal outer contour of the tool is determined and this deviation is allowed for when organizing the control of the blank machining operation. A parameter, for example, can be established for this purpose. A tool whose unsuitable condition has been recognized can, in such a case, be excluded from the machining process and new or other tools in better condition can carry out the task in hand.

All in all, it is to be emphasized that the gages can be positioned anywhere and, advantageously, are not only provided for the selection of the tool by reproducing the negative shape of the tool intended for machining in its ideal condition, but are also available for determining the wear condition of the tool. The exact position of the gage will be known to the machining equipment or is determined by it.

BRIEF DESCRIPTION OF THE DRAWINGS

The method of the invention is described with reference to the drawings, in which.

DESCRIPTION OF EXEMPLARY EMBODIMENTS OF THE INVENTION

Figure 1A:
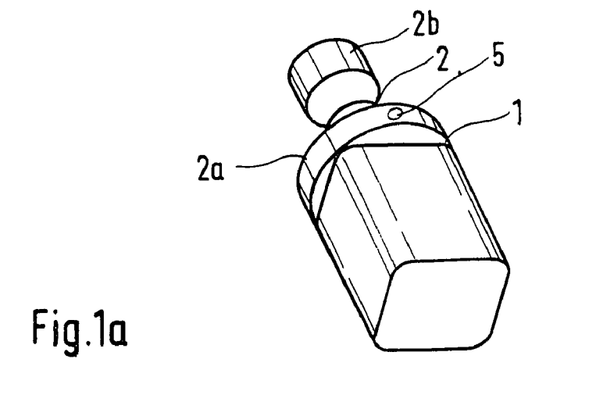
FIG. 1a is a perspective view of a first blank for the fabrication of a dental shaped body with a gage on a handle of a blank corpus.

The blank of FIG. 1a contains a corpus 1, which can consist of a material commonly used in dental technology, e.g. a ceramic material, but also of any other dimensionally stable material such as metal or plastics, from which the shaped body will be fabricated by means of a carving process. The corpus 1 of the blank is advantageously circular or rectangular in cross section. The front end of the corpus of the blank is adjoined by a cylindrical handle 2 in known manner, and the rear end includes a reference portion 6.

The material of the handle 2 can be identical with, or different from, that of the corpus 1. In the case of different materials, blank corpus 1 will be fastened to handle 2, for example by gluing. For this purpose, the handle 2 exhibits, for example, a circular cylindrical flange 2a having a diameter that is sufficient to ensure secure attachment to corpus 1, and a shaft 2b for insertion into the machining equipment. The shaft 2b is designed to fit into a predefined socket on the machining equipment.

Figure 1B:
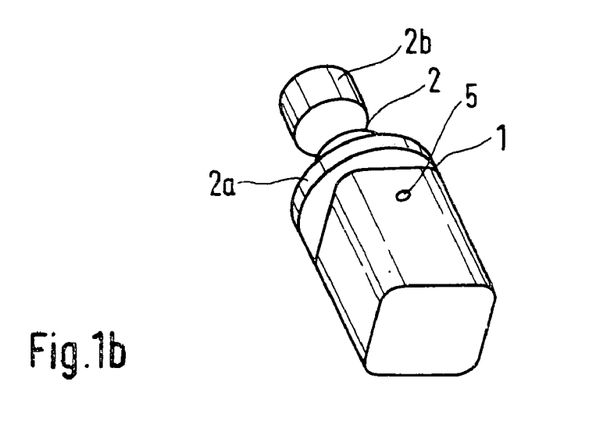
FIG. 1b is a perspective view of a further embodiment of a blank according to the invention with a gage on the blank corpus.
Figure 1C:
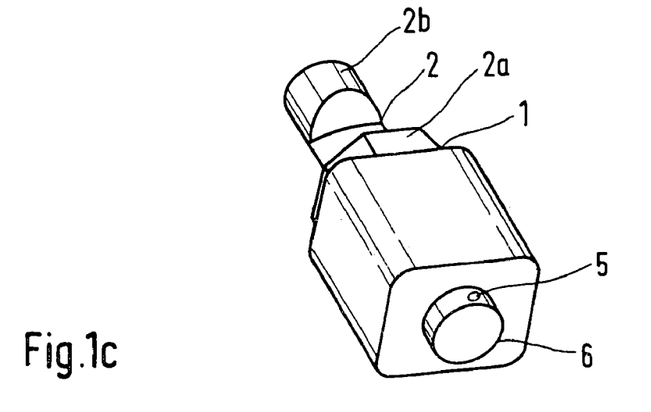
FIG. 1c is a perspective view of a further blank having at least one gage on a reference surface located on the blank.

In FIGS. 1a to 1c, a recess 5 having gaging properties is provided. Such recesses can be provided individually or in moderate numbers at various places of the blank. Due to their gaging properties, these recesses serve to select and evaluate the individual tools, since five specific sets of data of the tool, e.g., their dimensions, state of wear, and position, can be identified with the aid of the recesses 5.

Figure 2A:
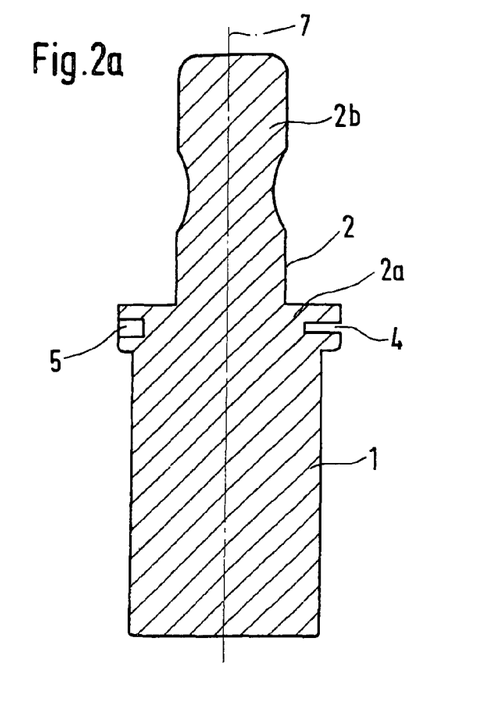
FIG. 2a is a longitudinal cross section of a blank in a first embodiment.

FIG. 2a shows a corpus 1 in a first embodiment. The blank corpus 1 has two gages 4, 5 which are disposed in diametrical opposition in the central region of the corpus of the blank 1. The gages 4, 5 are placed on the corpus 1 such that the blank can be clamped in machining equipment whilst the gages are still accessible to the tools on each side of the blank.

Figure 2B:
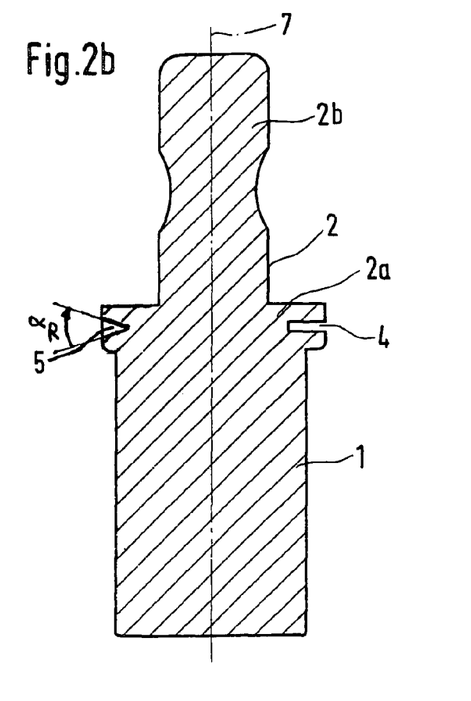
FIG. 2b is a longitudinal cross section of a blank in a second embodiment.

FIG. 2b illustrates an alternative corpus 1 which has a gage 5 that is tapered toward its base and whose conical envelope has an angle $\alpha_R$ which is greater than the angle of the conical envelope of the tool intended for recognition. If the aperture angle $\alpha_R$ of the conical envelope of the gage 5 is larger than that of the tool, the tool will be able to penetrate to the base of the gage 5 before it makes contact. Thus an unambiguous position is achieved when such a tool makes contact.

Figure 2C:
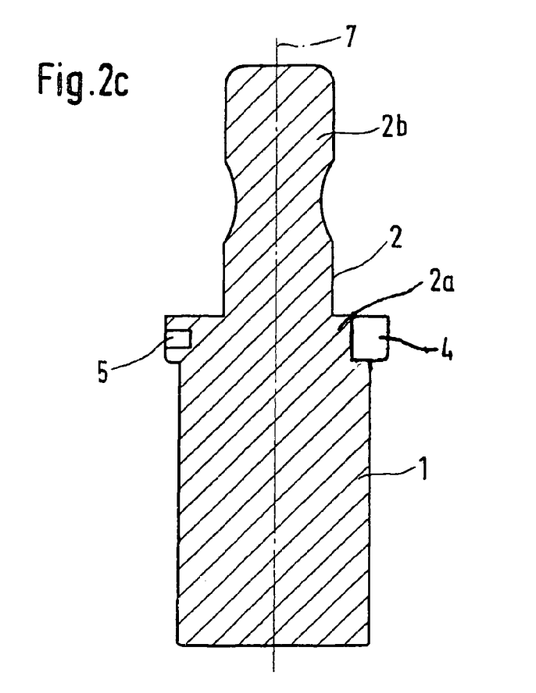
FIG. 2c is a longitudinal cross section of a blank in a third embodiment.

FIG. 2c illustrates another corpus 1 which has, in addition to the two cages 4, 5, yet another recess 4' that is disposed on the handle 2 of the blank. This recess 4' serves to place the blank 1 in an unambiguous position in machining equipment, since, when appropriate blank-holding means are provided in the machining equipment, the blank 1 can only be introduced into the blank-holding means in exactly one position. Furthermore, the recess 5' can be designed differently depending on the type of blank so that the machining equipment can recognize the type of blank by reference to this recess 4'.

Figure 3A:
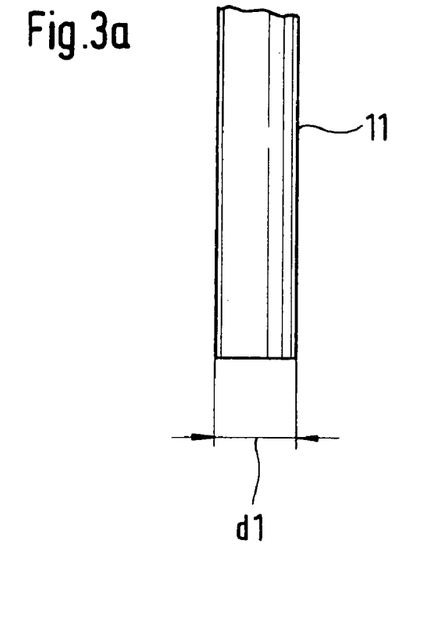
FIG. 3a shows a machining tool in the form of a diamond-coated cylindrical grinder having a first diameter.
Figure 3B:
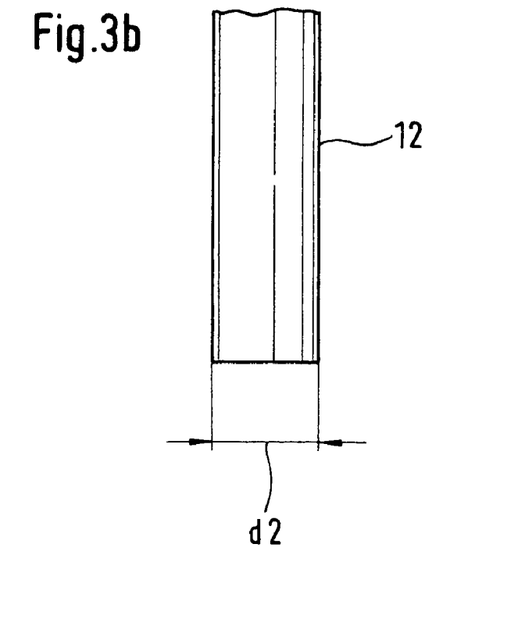
FIG. 3b shows a machining tool in the form of a diamond-coated cylindrical grinder having a second diameter.
Figure 3C:
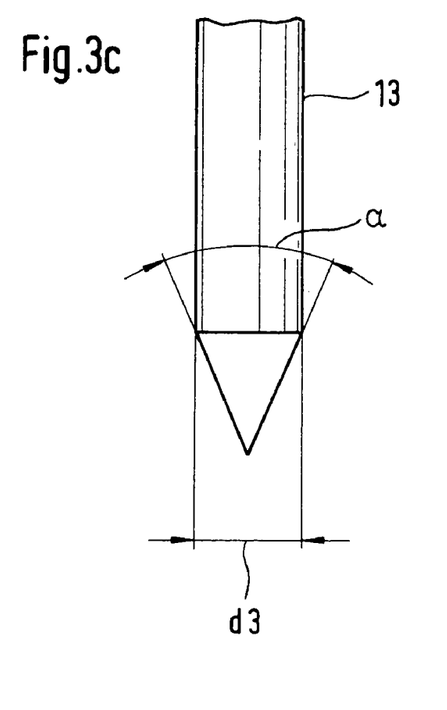
FIG. 3c shows a machining tool in the form of a diamond-coated grinder having a conical point.

FIGS. 3a-3c show machining tools as used for machining corpus 1. FIGS. 3a and 3b show a diamond-coated cylindrical grinder or milling cutter, with the grinder 11 of FIG. 3a exhibiting a first diameter d1 and the grinder 12 of FIG. 3b a second diameter d2. A grinder that is designed in this way is primarily used for machining interior spaces with vertical walls.

Figure 3D:
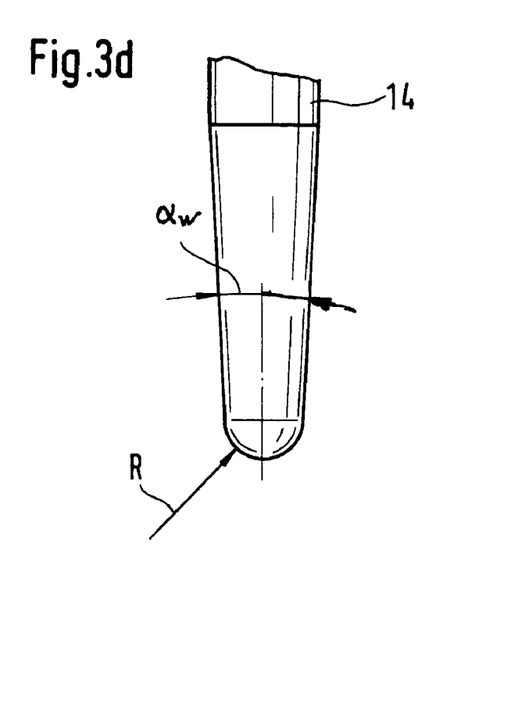
FIG. 3d shows a machining tool in the form of a diamond-coated grinder having a tapered portion and a rounded conical point.

FIGS. 3c and 3d each show a diamond-coated grinder 13, 14 that tapers to a point. In FIG. 3c, the end of the grinder 13 exhibits an angle α of 45°. In FIG. 3d the end of the grinder 14 is in the form of a cone, of which the point is rounded with a radius R. The angle $\alpha_W$ of the conical envelope of the grinder is in this case approximately 5°. A grinder that is shaped in this way is primarily used for machining occlusion surfaces with fissures, as well as interior spaces with non-vertical walls.

Figure 3E:
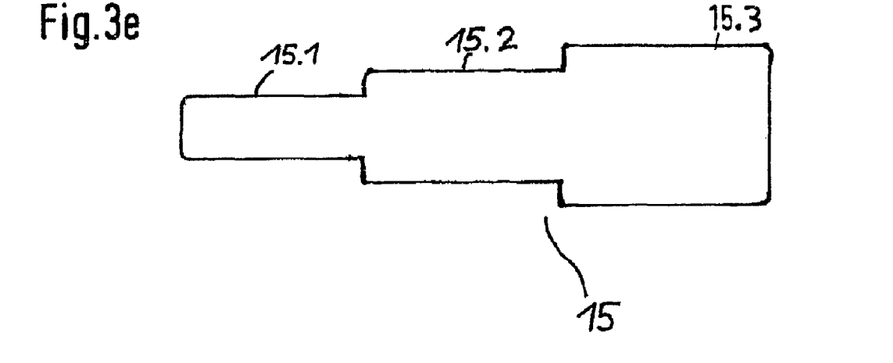
FIG. 3e shows a machining tool in the form of a diamond-coated grinder having several cylindrical grinding stages.

FIG. 3e shows a stepped grinder 15 having three stages 15.1, 15.2 and 15.3, which taper toward the final cutting edge. Each stage is cylindrical. Such a stepped grinder 15 is particularly well suited for the production of dental prosthetic items since they can be used for carving vertical lateral surfaces to a certain depth and the stepped grinder 15 operates more precisely because the fact that it bears vertically against the blank reduces its tendency to slide off, as compared with a conical grinder. A stepped grinder, when guided properly, nevertheless provides the same possibilities as a conical grinder.

Figure 4A:
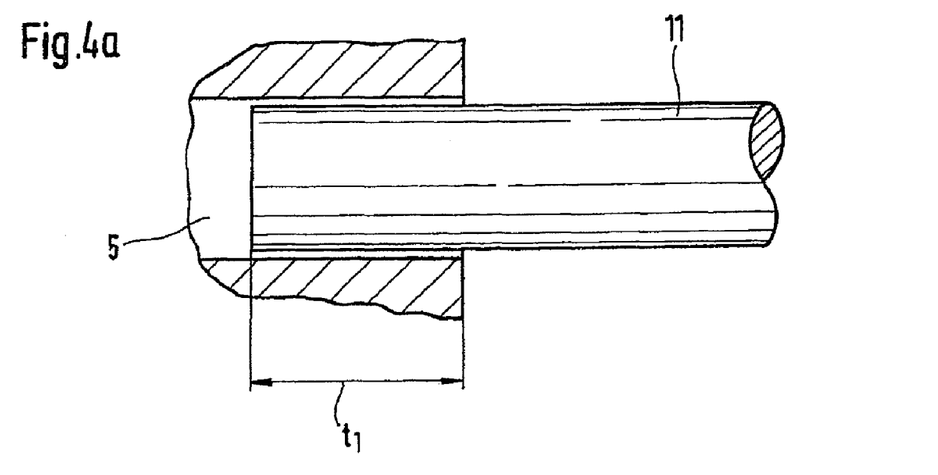
FIG. 4a shows a gage by means of which the machining tool of FIG. 3a is checked.
Figure 4B:
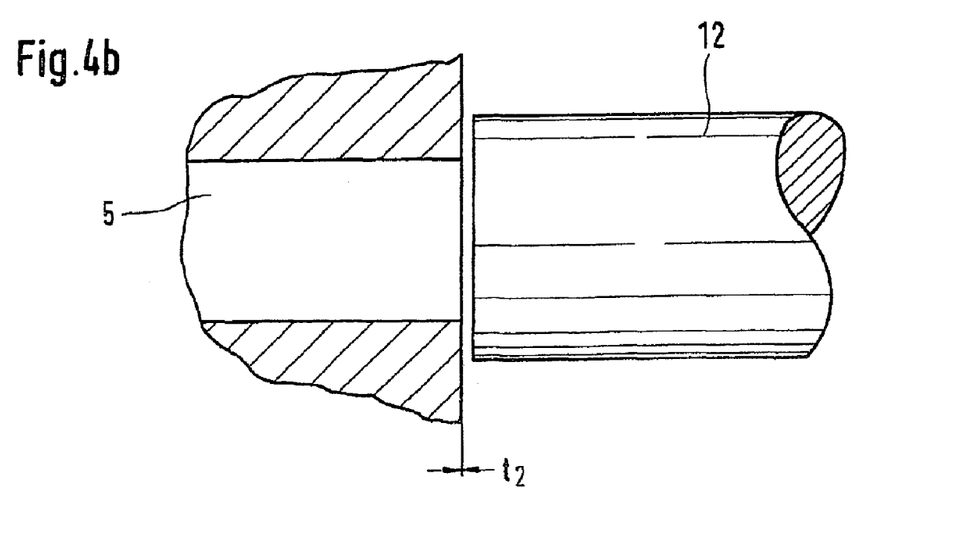
FIG. 4b shows a gage by means of which the machining tool of FIG. 3b is checked.

FIGS. 4a-4c show the machining tools of FIGS. 3a-3e engaged in a gage. FIGS. 4a and 4b show a diamond-coated cylindrical grinder 11, 12, and demonstrate how the grinder 11 penetrates the bore-shaped gage 5 by a distance t1, whilst the other grinder 12, because of its larger diameter, cannot penetrate gage 5. The penetration depth t2 is in this case equal to zero, from which it can be ascertained that the tool 12 is involved.

Figure 4C:
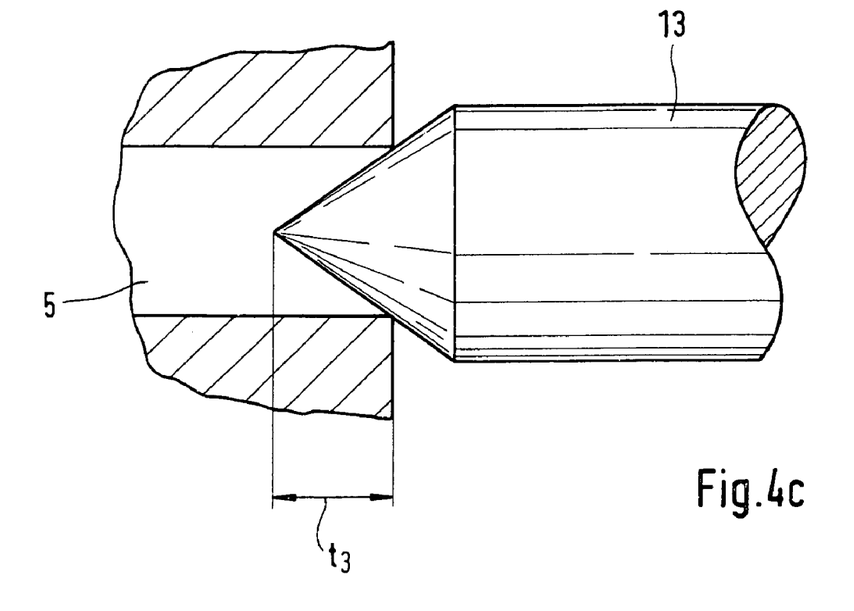
FIG. 4c shows a gage by means of which the machining tool of FIG. 3c is checked.
Figure 4D:
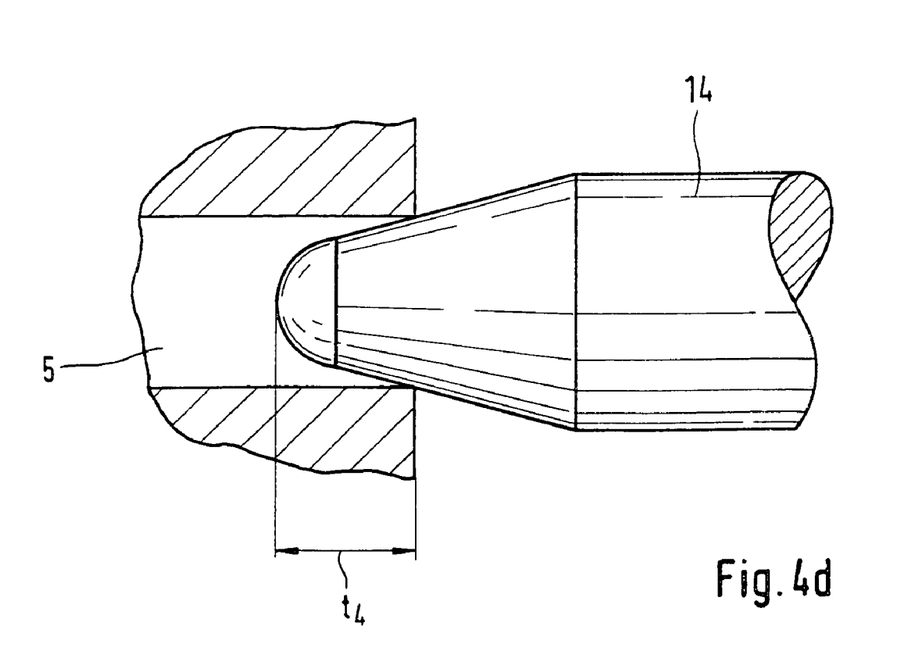
FIG. 4d shows a gage by means of which the machining tool of FIG. 3d is checked.

FIGS. 4c and 4d each show a diamond-coated grinder 13, 14 tapered to a tip as it penetrates gage 5 in the form of a bore. The penetrations illustrated in FIGS. 4c and 4d of a magnitude t3 in FIG. 4c and a magnitude t4 in FIG. 4d, serve not only to determine the ideal outer contour and thus to define the type of tool, but also provide information on the wear condition and the suitability of the respective tool for the intended machining process.

Figure 4E:
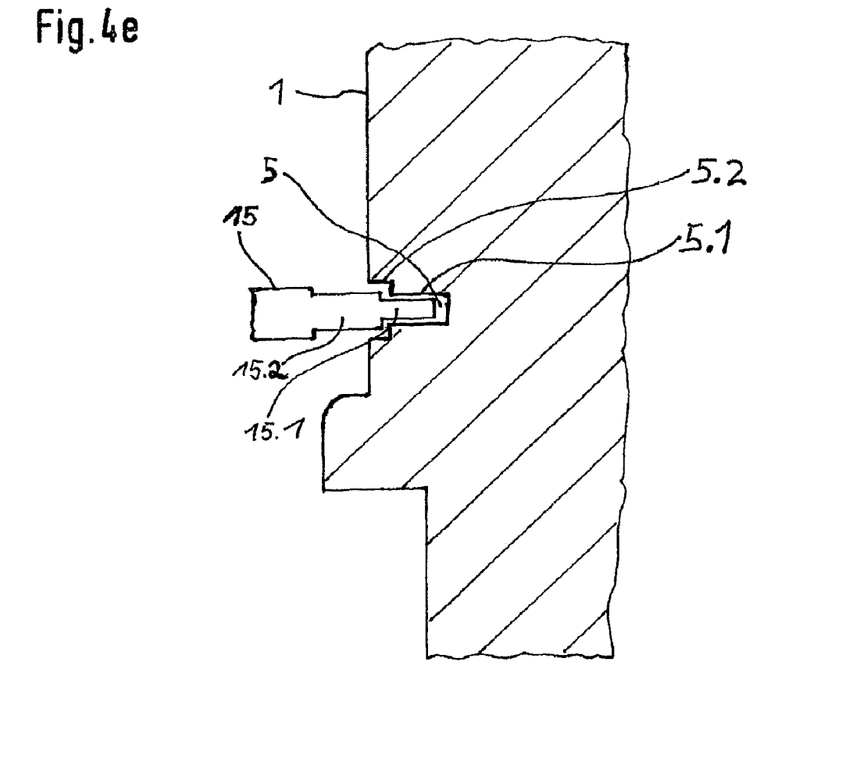
FIG. 4e shows a gage by means of which the machining tool of FIG. 3e is checked.

FIG. 4e shows a stepped grinder 15, which is being checked by a two-stage gage 5 provided for this purpose. The second stage 5.1 of the gage 5 is inside the first stage 5.2 and has a smaller diameter than the first stage 5.2. The diameter and the depth of the second stage 5.1 of gage 5 are dimensioned such that stage 15.1 at the cutting edge tip of the stepped grinder 15 can penetrate completely into the second stage 5.1 of the gage 5, which is not possible, however, for the second stage 15.2 of stepped grinder 15. The external, first stage 5.2 of gage 5 is dimensioned such that the second stage 15.2 of the stepped grinder 15 can enter it. The stepped grinder 15 contacts the gage 5 therefore with its front cutting surface of the second stage 15.2 of the stepped grinder 15 at the base of the first stage 5.2 of the gage 5. This ensures unambiguous recognition of the stepped grinder 15.

Figure 4F:
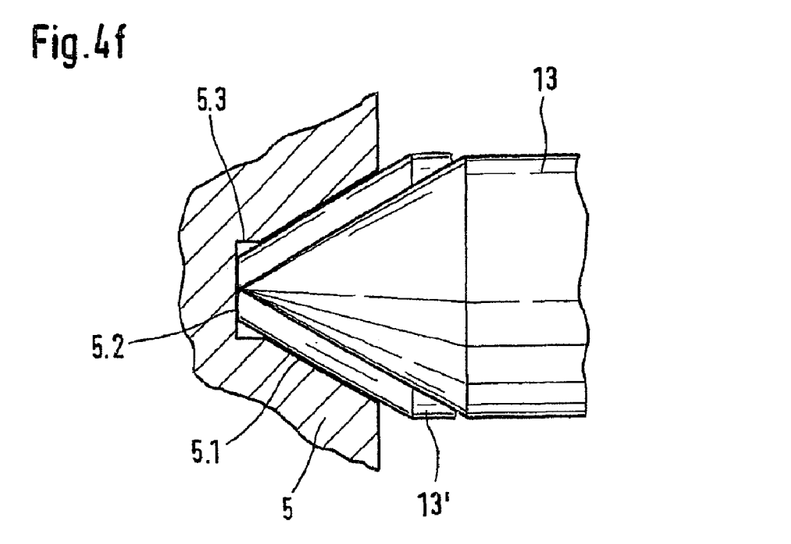
FIG. 4f shows another gage by means of which the machining tool of FIG. 3c is checked.

FIG. 4f shows a gage 5 that is used to detect the wear condition of the tool tip. The gage has a conical open region 5.1, which merges into a base region 5.2. Between them is a cylindrical region 5.3. Tool 13, when new, moves into the gage at its pointed end such that only the tip touches the base 5.2. If the tip is as worn out as on tool 13', then the depth of penetration of its pointed end up to the point of reaching the base 5.2 or up to the point of touching the side walls of the open region 5.1 will be greater than when the tool 13 is new. The amount of wear can thus be inferred from this measurement.

Figure 5:
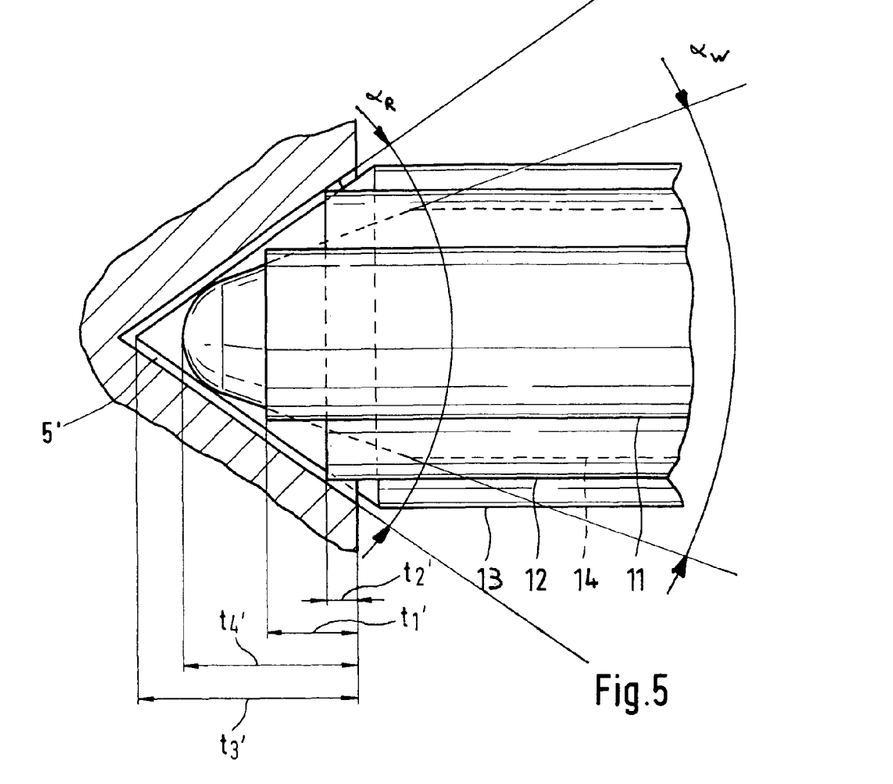
FIG. 5 shows a gage that is designed as a universal gage for checking several tools having various contours.

FIG. 5 shows a single cylindrical recess 5' for the tools 11 to 14 shown in FIGS. 3a to 3d, that is designed as a universal gage. The respective actual penetration depths t1', t2', t3', t4', provide information on the condition of the respective tool and thus on the suitability of the tool for the intended machining operation. The recess has an aperture angle $\alpha_R$ which is greater than the angle $\alpha_W$ of the conical envelope of conical grinder 14 and is equal to the cone angle (not shown) of the conical grinder 13.

Figure 6:
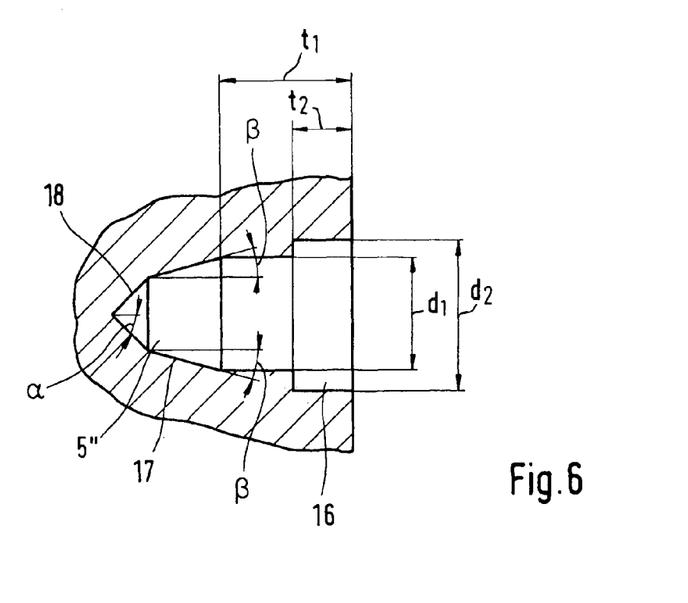
FIG. 6 shows a further embodiment of a gage suitable for use as a universal gage.

FIG. 6 shows a further single recess 5" serving as a universal gage. This recess includes a bore 16 having a diameter d2 and an associated possible penetration depth t2 and one having a diameter d1 and an associated possible penetration depth t2. In addition, the recess exhibits a taper 17 having a cone angle β and a further taper 18 having a cone angle α for the examination of corresponding tools. Alternatively, instead of one or more angles, one or more roundings having radii R (see FIG. 3d) that match the respective tools can be provided. The penetration depth achieved in each instance can yield information on the condition of the respective tool and thus the suitability thereof for the intended machining operation.

Figure 7A:
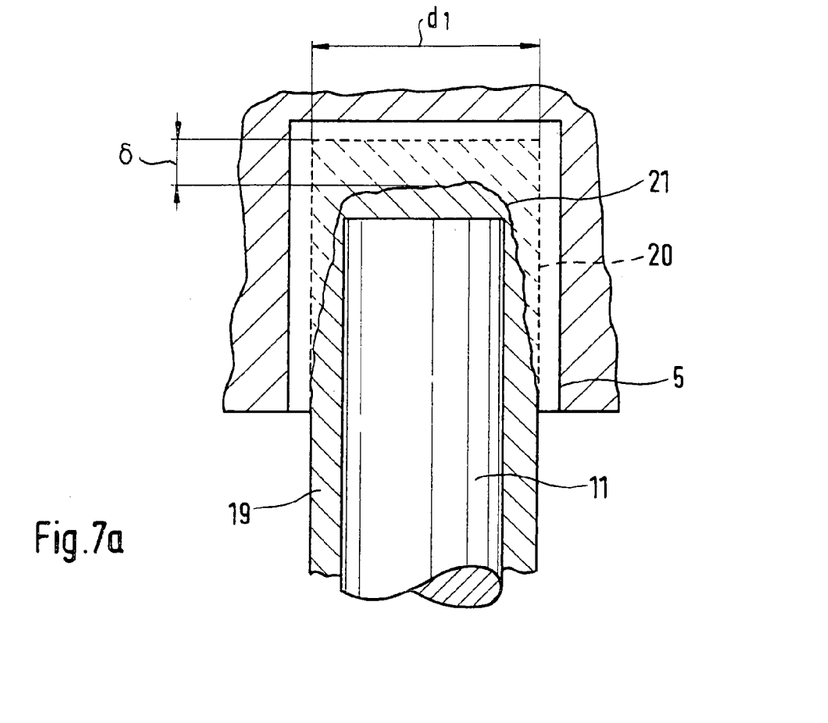
FIGS. 7a-7b show wear measurement means for a cylindrical and conical grinder respectively.
Figure 7B:
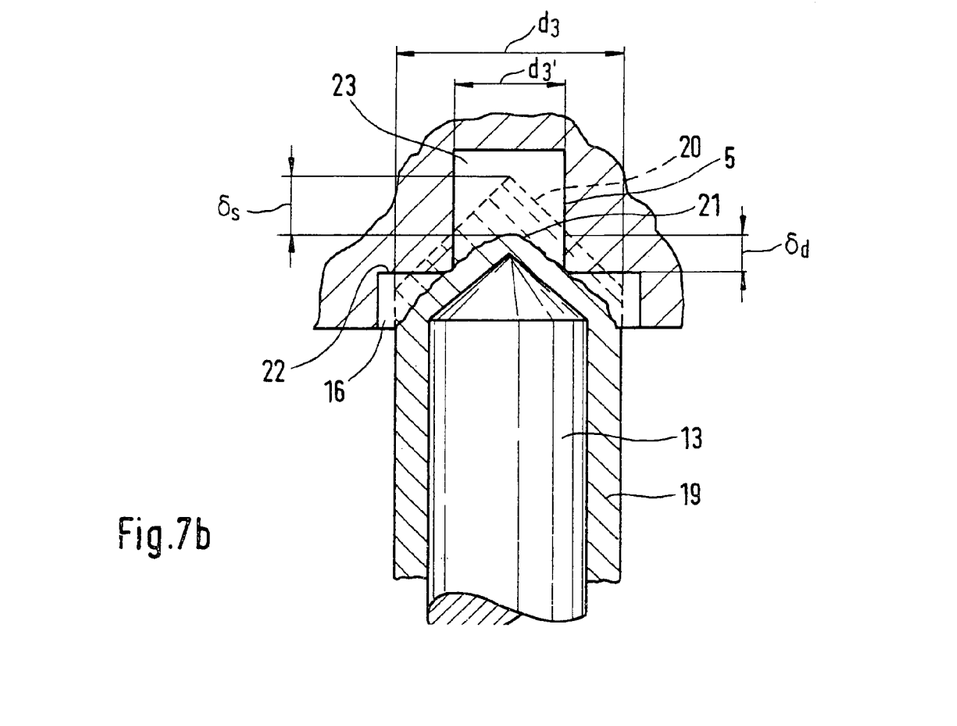

FIGS. 7a and 7b show how wear measurement can be carried out. Tool 11 is furnished with a coating 19 that provides the actual machining edges, for example the diamond coating of a grinding pin. This coating 19 exhibits an ideal outer contour 20, which is indicated by the dashed lines. However, due to the wear incurred during machining, the actual outer contour 21 of the tool 11 will deviate from the ideal outer contour 20.

In the region of the machining end-surface, the amount of wear of the coating 19 between the ideal outer contour 20 and the actual outer contour 21 is equal to the distance δ which, with an original coating thickness of from 50 to 60 μm, can well amount to from 40 to 50 μm. The wear of the machining end-surface can be determined by measuring the depth of penetration of tool 11 into gage 5.

FIG. 7b shows how a gage 5 can be used for measurement of the wear of a coated conical grinder. The conical grinder has a coating 19, which again has an ideal outer contour 20 and an actual outer contour 21. Due to the bore 16, the diameter of the used tool 13 is first identified and, due to a stop limit surface 22 having a central bore 23, the wear $\delta_d$ of the envelope of the cone is determined. The wear $\delta_s$ of the cone tip can be determined in accordance with FIG. 7a, but can also be measured in accordance with FIG. 7b when certain empirical values are available. For the measurement of a truncated cone point, and also of a conical grinder, a separate gage can be provided for each diameter, and the wear measurement can, in each case, be carried out by measuring the depth of penetration into the gage.

The invention claimed is:

1. A method for producing a dental-shaped body in a machine which utilizes at least one of a first tool and a second tool from a plurality of tools having differing outer contours, said method comprising the steps of:
   (a) providing a blank from which the dental-shaped body can be machined, said blank including a first gage and a second gage, the gages being in the form of a first recess and a second recess, respectively, the first recess having at least one predetermined dimension, the first recess pre-constructed to receive the first tool which is pre-constructed to fit into the first recess, such that the first tool is identified as the first tool, the second recess having at least one predetermined dimension, the second recess pre-constructed to receive the second tool which is pre-constructed to fit into the second recess, such that the second tool is identified as the second tool, and
   (b) machining said body with at least one of said identified first tool and said identified second tool to provide said machined body.

2. The method as defined in claim 1, wherein the first tool is at least one of a grinder and a cutter, and wherein the second tool is at least one of a grinder and a cutter.

3. The method as defined in claim 1, wherein the actual state of the first tool and the degree of deviation of the actual state of the first tool are determined based on a depth of penetration of the first tool into the first recess, and
   wherein the actual state of the second tool and the degree of deviation of the actual state of the second tool are determined based on a depth of penetration of the second tool into the second recess.

4. The method as defined in claim 1, wherein the first tool penetrates the first recess and an actual state of dimensions of the first tool is determined, and wherein the second tool penetrates the second recess, and an actual state of dimensions of the second tool is determined.

5. The method as defined in claim 4, wherein a degree of deviation of the actual state of the first tool from an ideal outer contour of said first tool is determined and the degree of deviation of the first tool is compensated for machining of said blank, wherein a degree of deviation of the actual state of the second tool from an ideal contour of said second tool is determined and the degree of deviation of the second tool is compensated for machining said blank.

* * * * *